(12) United States Patent
Kast et al.

(10) Patent No.: US 8,267,687 B2
(45) Date of Patent: Sep. 18, 2012

(54) CASTING ABUTMENT WITH IMPROVED GEOMETRY

(75) Inventors: Holger Kast, Lörrach (DE); Daniel Günter, Waldenburg (CH)

(73) Assignee: Straumann Holding AG, Basel (CH)

( * ) Notice: Subject to any disclaimer, the term of this patent is extended or adjusted under 35 U.S.C. 154(b) by 0 days.

(21) Appl. No.: 11/986,752

(22) Filed: Nov. 26, 2007

(65) Prior Publication Data
US 2008/0166680 A1 Jul. 10, 2008

(30) Foreign Application Priority Data
Nov. 27, 2006 (EP) ..................................... 06124797

(51) Int. Cl.
*A61C 13/12* (2006.01)
*A61C 13/225* (2006.01)

(52) U.S. Cl. ........................................................ 433/172

(58) Field of Classification Search .................. 433/172, 433/173, 174, 175, 176
See application file for complete search history.

(56) References Cited

U.S. PATENT DOCUMENTS 4,758,161 A * 7/1988 Niznick .......................... 433/173
5,259,759 A * 11/1993 Jorneus et al. ................. 433/173

* cited by examiner

*Primary Examiner* — Cris L Rodriguez
*Assistant Examiner* — Eric Rosen
(74) *Attorney, Agent, or Firm* — Scully, Scott, Murphy & Presser, P.C.

(57) ABSTRACT

Casting abutment for a dental implant that includes an apical socket portion, a transition portion bordering coronally on the socket portion, and an occlusal portion bordering coronally on the transition portion, having an apical circumferential collar area. The collar area is provided with an axially closer lying first circumferential platform and with at least two adjacent circumferential step-like areas, wherein the largest diameter of a first step-like area is smaller than the smallest diameter of a second step-like area the second step-like area lying apically with respect to the first step-like area.

4 Claims, 1 Drawing Sheet

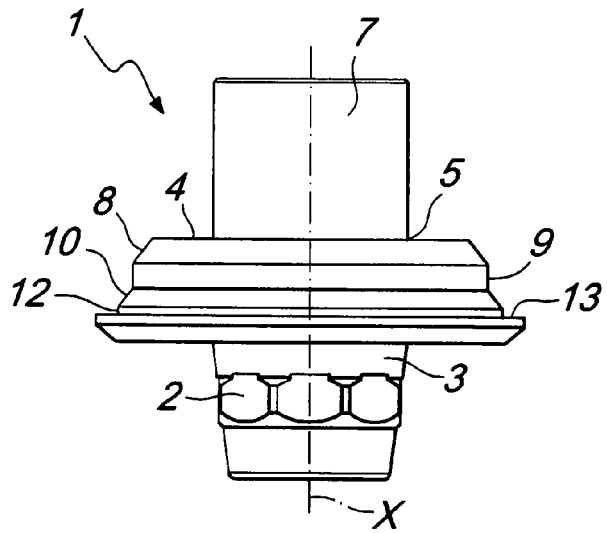 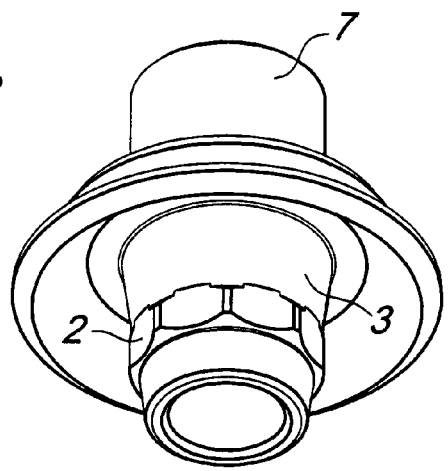
Fig. 1A
Fig. 1B
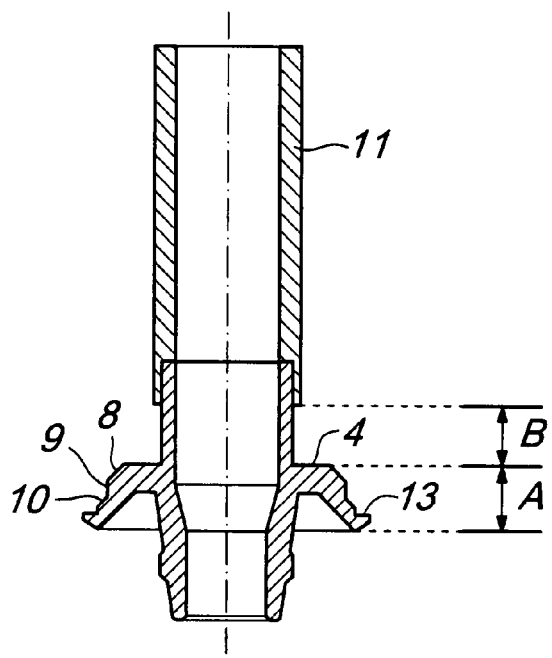 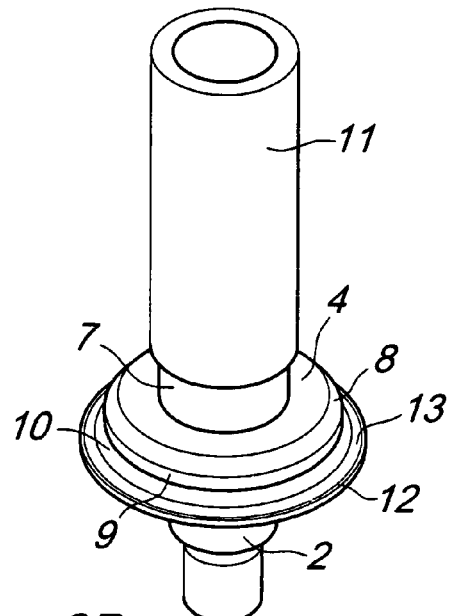
Fig. 2A
Fig. 2B

CASTING ABUTMENT WITH IMPROVED GEOMETRY

The present invention refers generally to a casting abutment for a dental implant with improved geometry and in particular to a casting abutment for a dental implant with improved geometry which is suitable for manufacturing a dental prosthesis from a precious metal, such as gold, or from a metal alloy by means of a lost wax process.

BACKGROUND OF THE INVENTION

In the art of dentistry, casting abutments for receiving a dental prosthesis have become widely known. A structure (dental prosthesis) modeled after the natural tooth is mounted on the occlusal portion of the casting abutment. This structure is then mechanically attached to a dental implant, in most cases similar to a dowel pin, which was previously implanted in a patient's jaw bone.

As is well-known, such structures are manufactured as follows. First, a wax model is modeled on the casting abutment according to the shape of the natural tooth to be replaced. In most cases, the wax model is produced using a modeling aid made of plastics and plugged onto the casting abutment, which facilitates machining and keeps the access channel for the occlusal screw free. At the end of modeling, a structure made of wax has been created on the casting abutment.

Subsequently, the casting abutment with the wax structure modeled on top of it is embedded in an encapsulant. During heating of the mold, which is necessary for the casting process, the wax of the dental model and the modeling aid evaporate without leaving any residue. Thus, the negative mold is created which is later filled with a precious metal, such as gold, or a precious metal alloy (in the following termed precious metal for the sake of simplicity). In this way, a metal model is created which corresponds to the wax structure modeled on top of the casting abutment (in the following called casting model for the sake of simplicity).

The above method is called lost wax method, as is well-known in the art.

After the casting model has been created, it is normally veneered with a ceramic layer in order to achieve as realistic as possible a reproduction of the tooth to be replaced.

It has turned out that during manufacturing of the casting model by means of the conventional lost wax method, the precious metal can overflow under the collar area of the casting abutment, which would lead to undesired effects such as casting blisters. The overflow is due to the fact that surfaces of the casting abutment have not been sufficiently cleaned. Casting defects can lead to an imprecise fit or formation of a gap between casting abutment and dental implant. Such faulty casting models cannot be used, due to the high demands made on a precise connection between the casting abutment and the dental implant and the long-term demands made on dental prostheses, and must be re-manufactured.

In addition, with straight running collar areas of casting abutments (i.e. collar areas running vertically to the longitudinal axis of the casting abutment), it is especially problematic that these abutments have a tendency towards frequent overflow or excess of the molten precious metal, which has been heated up to high temperatures and cast. This is due, among others, to unfavorable flow characteristics of the molten precious metal on the collar area of the casting abutment.

As a remedy to the above-mentioned problem, normally a layer of graphite is applied in those areas where it is desired to stop the flow of the molten precious metal. The disadvantage of this procedure, however, is that graphite particles can contaminate the precious metal in the contact areas between the precious metal and the area covered by graphite.

Therefore, it is desirable to provide an improved casting abutment which can offer a perfect connection between the casting model and the dental implant even after casting. This is of special importance since the high compressive forces generated during chewing place immensely high requirements on the materials used and the precise fit which form the connection between casting model and dental implant. Minor errors during model manufacturing and during the gating process can lead to a metal model of the dental prosthesis which is no longer usable or must be refinished at considerable effort. Any cracks, contaminations, gaps or bruises must be avoided as well since they impair the mechanical long-term strength.

SUMMARY OF THE INVENTION

Therefore, it is an object of the present invention to provide for a casting abutment with an improved geometry for a dental implant which avoids the above-mentioned problems.

Within this aim, it is a special object of the present invention to implement a casting abutment for a dental implant which causes the slowdown of the gated precious metal of the dental prosthesis.

In addition, it is a special object of the present invention to provide a casting abutment for a dental implant which ensures optimized flow characteristics of the molten precious metal.

It is a further object of the present invention to implement a casting abutment which minimizes the use of graphite as a barrier or blockage for the molten precious metal. Thus, graphite can be avoided except for small areas of application.

The above-mentioned aims and objects as well as other objects to be found in the following specification are fulfilled by a casting abutment according to appended claim 1. Advantageous further developments of the present invention are subject of the dependent claims.

BRIEF DESCRIPTION OF THE DRAWINGS

Other features and advantages of the present invention as well as the method of functioning of the exemplary embodiment of the present invention are described below with reference to the accompanying drawings which exemplify the present invention and are further used, together with the specification, to explain the principles of the invention and enable the person skilled in the art to manufacture and use the invention. In the drawings:

FIG. 1A shows a side or approximal view of a casting abutment according to a preferred embodiment of the invention;

FIG. 1B shows a view of FIG. 1A from below at an angle;

FIG. 2A shows an approximal view of a casting abutment of FIG. 1A in full section with the modeling aid plugged on;

FIG. 2B shows a top view of FIG. 2A at an angle.

DESCRIPTION OF PREFERRED EMBODIMENTS

With reference to FIGS. 1A and 1B, a currently preferred embodiment of the casting abutment for a dental implant with improved geometry according to the present invention is described. The casting abutment generally designated by reference number 1 has an apical socket portion 2, a transition portion 3 bordering coronally on the socket portion 2 and on which coronally borders an occlusal portion 7 with an apical, circumferential collar area A, the collar area A being adapted with an axially closer lying first platform 4 and with at least two adjacent circumferential step-like areas 8, 9 and 10, 12, respectively, which together form a collar surface, wherein the largest diameter of the first step-like area 8, 9 is smaller than the smallest diameter of a second step-like area 10, 12, the second step-like area 10, 12 laying apically in respect to the first step-like area 8, 9. In other words, the two step-like areas 8, 9 and 10, 12, respectively, act as a stair extending radially outwards from the first platform.

The occlusal portion 7 is rotationally symmetric and has a substantially cylindrical form. The first platform 4 extends substantially in the horizontal direction adjoining to the occlusal portion 7, the first platform 4 bordering on the medial side to an outer edge 5 of the occlusal portion 7 cylindrical form and being substantially flat. The first platform 4 is preferably at an angle of 80 to 100° in respect to the longitudinal axis of the casting abutment 1 and, even more preferably, an angle of about 90° in respect to the longitudinal axis of the casting abutment 1.

On its distal side, the first platform 4 merges into a first beveled section 8 of the first step-like area 8, 9, inclined downwardly preferably at an angle of 35 to 55° and, even more preferably, of about 45° in respect to the longitudinal axis of the casting abutment 1. In a preferred embodiment, the first platform 4 is 1.5 to 2 times as wide as the total height of the first step-like area 8, 9.

The edge of the first beveled section 8 borders on a first vertical section 9 substantially parallel to the longitudinal axis of the casting abutment 1. The height of the first vertical section 9 is approximately the same as that of the first beveled section 8 above it.

The first vertical section 9 merges into a second beveled section 10 of the second step-like area 10, 12, which is also inclined downwardly preferably at an angle of 35 to 55° and, even more preferably, at an angle of 45° in respect to the longitudinal axis of the casting abutment 1, and on which borders a second vertical section 12 substantially parallel to the longitudinal axis of the casting abutment 1 and having a height of approximately 25% of that of the first vertical section 9.

Bordering directly on the second vertical section 12, there is preferably a second platform 13 having a width of approximately one third of the first platform 4. The second platform 13 also extends in the horizontal direction and is substantially level. Analogously to the first platform 4, the second platform 13 is preferably at an angle of 80 to 100° in respect to the longitudinal axis of the casting abutment 1 and even more preferably at an angle of about 90° in respect to the longitudinal axis of the casting abutment 1. If there is a second platform 13, it is also part of the collar area.

FIGS. 2A and 2B show the casting abutment 1 according to the invention with the plugged-on cylindrical modeling aid 11 which is made of plastics which can be burnt out and is readily placed on the casting abutment 1, in different views. Plastics must always be covered by wax of a certain thickness which, in the muffle, is used as a "buffer" against swelling of the plastics during the process of burning out. Without such a "buffer", the encapsulant might burst. Therefore, the prefabricated plastics channel is plugged over the gold casting portion only to a certain depth in the occlusal area, in order to leave enough space for as much individual wax modeling as possible in the casting portion lower area (area B). Within the collar area designated by reference number A, the two platforms 4, 13 and the at least two step-like areas 8, 9 and 10, 12, respectively, are arranged which enable the liquid metal alloy to flow around the collar area very evenly when it is gated through a channel in the encapsulant (not shown).

The layers, acting like stairs, formed by the platforms 4, 13 and the step-like areas 8, 9 and 10, 12, respectively, thus also slowdown the flowing of the molten precious metal to the end portions of the casting abutment 1 and avoid the application of any barriers, such as, for instance, graphite. The first platform 4 is advantageously configured wider in order to provide a large contact surface between the molten precious metal and the occlusal portion 7 and the first platform 4. The step-like areas 8, 9 and 10, 12, respectively, advantageously reduce the amount of precious metal to be applied since it only has to be applied in the outer areas. The step-like areas 8, 9 and 10, 12, respectively, cause the wall thickness of the metal model to be relatively homogeneous throughout the collar area, which is also effective in reducing the thermal shock, when the enclosed strongly heated molten precious metal impacts the relatively cool collar area, thus avoiding a deformation of the casting abutment 1.

Although the invention has been described in connection with a one-piece casting abutment, the person skilled in the art will readily understand that it also applies to two-piece casting abutments, with naturally the same advantages being achieved as in connection with a one-piece casting abutment. Also, the number of step-like areas can be increased as compared to that of the shown embodiment. In practice, good results have also been achieved with three, four or five step-like areas. Indeed, it is in practice desirable to maximize the number of step-like areas, although it is necessary to select their number taking into account the available space and manufacturing requirements, as is known to the person skilled in the art.

The disclosures in EPA No. 06124797.9 from which this application claims priority are incorporated herein by reference.

What is claimed is:

1. A casting abutment for a dental implant, said casting abutment comprising:
   an apical socket portion;
   a transition portion bordering coronally on the socket portion; and
   an occlusal portion bordering coronally on the transition portion, the occlusal portion comprising a coronal end and an apical circumferential collar area, the collar area being provided with an outwardly extending circumferential platform having a greater diameter than said coronal end and with at least two adjacent circumferential step areas apical of the circumferential platform and extending radially outward therefrom, wherein the circumferential platform extends between an outer edge and a medial edge, the medial edge bordering on an outer edge of the coronal end for allowing wax to be supported on the circumferential platform, wherein the circumferential platform is completely unobstructed in the occlusal direction between the outer edge of the circumferential platform and the medial edge of the circumferential platform,
   wherein the at least two adjacent circumferential step areas comprises a first step area and a second step area, the second step area lying apically adjacent in respect to the first step area and wherein the smallest diameter of the second step area is no smaller than the largest diameter of the first step area.

2. The casting abutment according to claim 1, wherein each step area is provided in respect to the longitudinal axis of the casting abutment with a beveled section and with a substantially vertical section.

3. The casting abutment according to claim 2, wherein the first beveled section of the first step area and/or the second beveled section of the second step area is inclined at an angle of 35 to 55° in respect to the longitudinal axis of the casting abutment.

4. The casting-abutment according to claim 3, wherein the angle of the first beveled section is of about 45° and/or the angle of the second beveled section is of about 45°.

* * * * *